United States Patent [19]

Simon

[11] Patent Number: 5,439,897
[45] Date of Patent: Aug. 8, 1995

[54] AZOXYCYANOBENZENE DERIVATIVES, COMPOSITIONS CONTAINING THEM AND THEIR USE AS FUNGICIDES

[75] Inventor: Werner E. J. Simon, Heilbronn, Germany

[73] Assignee: American Cyanamid Company, Wayne, N.J.

[21] Appl. No.: 291,270

[22] Filed: Aug. 16, 1994

[30] Foreign Application Priority Data

Aug. 18, 1993 [EP] European Pat. Off. ........... 93113190

[51] Int. Cl.$^6$ .................. A01N 51/00; C07C 291/08
[52] U.S. Cl. .................. 514/149; 534/556; 534/558; 534/566; 534/572
[58] Field of Search ............ 534/556, 558, 566; 514/150, 149

[56] References Cited

U.S. PATENT DOCUMENTS

| | | | |
|---|---|---|---|
| Re. 24,960 | 4/1961 | Urbschat et al. | 534/558 X |
| 1,909,851 | 5/1933 | Zitscher et al. | 534/558 |
| 3,819,609 | 6/1974 | Puklics et al. | 534/556 |
| 4,550,121 | 10/1985 | Pilgram et al. | 514/469 |
| 4,558,040 | 12/1985 | Pilgram et al. | 514/150 |
| 4,883,137 | 5/1989 | Gilkerson et al. | 514/224.2 |
| 5,089,486 | 2/1992 | Wood et al. | 534/566 X |
| 5,298,606 | 3/1994 | Wood et al. | 534/556 |

FOREIGN PATENT DOCUMENTS

| | | |
|---|---|---|
| 0245902 | 11/1987 | European Pat. Off. . |
| 0411716 | 2/1991 | European Pat. Off. . |
| 0411720 | 2/1991 | European Pat. Off. . |
| 52-71444 | 6/1977 | Japan .................. 514/149 |
| 9412470 | 6/1994 | WIPO .................. 534/566 |

OTHER PUBLICATIONS

Y. Umeda, et al., *Antimicrobial phenylazoxycyanides*, Chemical Abstracts, 87:167770 (1977).
V. Mortarini, et al. *Synthesis, antibacterial and antifungal activity of phenylazoxycyanide derivatives*, Eur. J. Med. Chem., Chimica Therapeutica, 12(1), 1977 pp. 59–62.

Primary Examiner—Robert W. Ramsuer
Assistant Examiner—Fiona T. Powers
Attorney, Agent, or Firm—Charles F. Costello, Jr.

[57] ABSTRACT

This invention relates to certain azoxycyanobenzene derivatives of the general formula.

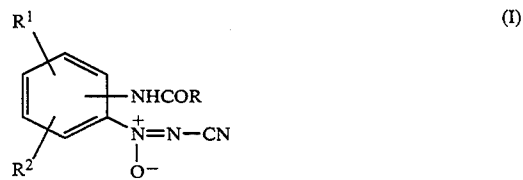

in which R represents an optionally substituted alkyl, alkenyl, alkynyl, cycloalkyl, cycloalkenyl, aryl or heterocyclyl group; $R^1$ represents a halogen atom, nitro, cyano or optionally substituted alkyl, alkoxy, aryl or aryloxy group; and $R^2$ represents a hydrogen or halogen atom, nitro, cyano or optionally substituted alkyl or alkoxy group; process for their preparation, compositions containing such compounds and their use as fungicides.

9 Claims, No Drawings

AZOXYCYANOBENZENE DERIVATIVES, COMPOSITIONS CONTAINING THEM AND THEIR USE AS FUNGICIDES

This invention relates to certain azoxycyanobenzene derivatives, processes for their preparation, compositions containing such compounds and their use as fungicides.

EP-A-0411716 discloses fungicidal compositions which comprise a carrier and, as active ingredient, a compound of the general formula $$R-N=NX \qquad (A)$$

or an N-oxide thereof, wherein R represents a substituted phenyl group, at least one substituent thereof being a group of general formula $-NR^1COR^2$ where $R^1$ represents a hydrogen atom or an alkyl group, and $R^2$ represents a hydrogen atom or an optionally substituted alkyl, alkoxy, alkenyl, alkenyloxy, phenyl or phenoxy group; and X represents a cyano group, a group —COOH or a salt, ester or amido derivative thereof. However, in each of the examples, the substituted phenyl group R bears only one substituent, that being of formula $-NR^1COR^2$.

It has now been discovered that certain azoxycyanobenzene derivatives, which bear at least two substituents on the benzene ring in addition to the azoxycyano group, exhibit good activity against certain phytopathogenic fungi.

According to the present invention there is therefore provided a compound of the general formula

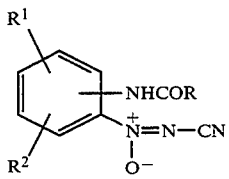

(I)

in which R represents an optionally substituted alkyl, alkenyl, alkynyl, cycloalkyl, cycloalkenyl, aryl or heterocylyl group; $R^1$ represents a halogen atom, nitro, cyano or optionally substituted alkyl, alkoxy, aryl or aryloxy group; and $R^2$ represents a hydrogen or halogen atom, nitro, cyano or optionally substituted alkyl or alkoxy group.

When the compounds of this invention contain an alkyl, alkenyl or alkynyl substituent group, this may be linear or branched and may contain up to 12, preferably up to 6 and especially up to 4, carbon atoms. Cycloalkyl or cycloalkenyl groups may contain 3 to 8, preferably 3 to 6, carbon atoms. An aryl group may be any aromatic hydrocarbon group, especially a phenyl or naphthyl group. A heterocyclyl group may be any saturated or unsaturated ring system containing at least one heteroatom, 3- to 6-membered rings being preferred and 5- and 6-membered rings being especially preferred. Nitrogen-, oxygen- and sulphur-containing heterocyclic rings, such as pyridyl, pyrimidinyl, pyrrolidinyl, furyl, pyranyl, morpholinyl and thienyl, are particualarly preferred.

When any of the foregoing substituents are designated as being optionally substituted, the substituent groups which are optionally present may be any one or more of those customarily employed in the development of pesticidal compounds, and/or the modification of such compounds to influence their structure/activity, persistence, penetration or other property. Specific examples of such substituents include, for example, halogen atoms, nitro, cyano, hydroxyl, alkyl, haloalkyl, alkoxy, haloalkoxy, amino, alkylamino, dialkylamino, formyl, alkoxycarbonyl, carboxyl, alkanoyl, cycloalkyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms. Typically, 0–3 substituents may be present, most commonly 0 or 1.

Preferably, R represents a $C_{1-6}$ alkyl, $C_{2-6}$ alkenyl, $C_{2-6}$ alkynyl, $C_{3-8}$ cycloalkenyl or phenyl group or a 3- to 6- membered heterocyclic ring, each group or ring being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, $C_{1-4}$ alkoxycarbonyl and $C_{3-8}$ cycloalkyl groups.

More preferably, R represents a $C_{1-6}$ alkyl, $C_{2-4}$ alkenyl, $C_{3-6}$ cycloalkenyl or phenyl group or a 5- to 6- membered heterocyclic ring (especially an oxygen-containing ring), each group or ring being optionally substituted by one or more substituents selected from halogen (especially fluorine and chlorine) atoms, $C_{1-4}$ alkoxy, $C_{1-4}$ alkoxycarbonyl and $C_{3-6}$ cycloalkyl groups.

It is preferred that $R^1$ represents a halogen atom, a nitro or cyano group, or a $C_{1-6}$ alkyl or $C_{1-6}$ alkoxy group each optionally substituted by one or more substituents selected from halogen atoms, nitro, cyano, hydroxyl and amino groups.

More preferably, $R^1$ represents a halogen (especially chlorine) atom, a cyano group, or a $C_{1-4}$ alkyl (especially methyl) or $C_{1-4}$ alkoxy (especially methoxy) group each optionally substituted (but preferably unsubstituted) by one or more halogen (especially fluorine or chlorine) atoms.

It is also preferred that $R^2$ represents a hydrogen or halogen (especially chlorine) atom.

Preferably, the group —NHCOR is attached to the 3- or, especially, 4- position of the benzene ring in the azoxycyanobenzene moiety. It is also preferred that $R^1$ is attached at the 4- or, especially 3- position and that $R^2$ is attached at the 5- position.

A particularly preferred sub-group of compounds of formula I is that in which R represents a methyl, ethyl, propyl, butyl, pentyl, chloromethyl, chloroethyl, bromoethyl, ethoxycarbonyl-methyl, cyclopentylethyl, propenyl, trimethylcyclohexenyl, difluorophenyl, trimethoxyphenyl or furanyl group; $R^1$ represents a chlorine atom or a cyano, methyl or methoxy group; and $R^2$ represents a hydrogen or chlorine atom.

It should also be noted that compounds of general formula I could be in any of the following isoelectronic forms:

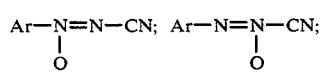

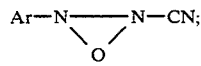

where Ar represents

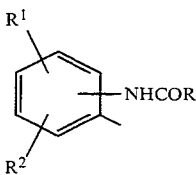

and the scope of the present invention covers all such forms.

The present invention also provides a process for the preparation of a compound of formula I as defined above which comprises treating a compound of general formula

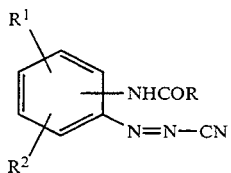

in which R, $R^1$ and $R^2$ are as defined above, with a mixture comprising hydrogen peroxide and methanoic acid and/or with peroxymethanoic acid.

Where a mixture of hydrogen peroxide and methanoic acid is used, the concentration of the hydrogen peroxide is suitably less than about 75 wt %, preferably less than about 50 wt % and, more preferably, less than 40 wt %. In a preferred embodiment the concentration of hydrogen peroxide is about 30 wt %.

The process is preferably carried out at or above, more preferably, above, ambient temperature. The process may be carried out at a temperature in the range from 25° C. to 75° C., preferably in the range from 30° C. to 50° C.

Preferably, the compound of general formula II is mixed with methanoic acid and hydrogen peroxide at ambient temperature. The mixture is preferably then heated, suitably at about 60° C., for a number of hours. The mixture may then be cooled, for instance, in an ice bath. The desired product may then be isolated by standard techniques.

A general process for the preparation of compounds of formula II is provided by R. J. W. LeFevre and H. Vine, J. Chem. Soc., (1938), 431.

The present invention further provides an alternative process for the preparation of a compound of formula I as defined above which comprises reacting a compound of general formula

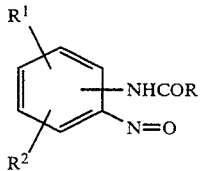

in which R, $R^1$ and $R^2$ are as defined above, with cyanamide or a metal salt thereof and an oxidising agent.

The oxidising agent may be any compound which, in conjunction with cyanamide or a metal salt thereof, generates a cyanonitrene. Preferred examples include iodobenzene diacetate, dibromoisocyanuric acid and cyclic or linear N-halogen or pseudohalogen amides or imides, especially N-bromosuccinimide.

If a metal salt of cyanamide is used in the process of the invention, it is preferred that the metal salt is an alkali metal salt or an alkaline earth metal salt. Alternatively, such metal salts can be generated in situ by reacting cyanamide with an alkali metal hydroxide or an alkaline earth metal hydroxide. The use of monosodium cyanamide is especially preferred. Alternatively, this may be replaced by a concentrated aqueous solution of cyanamide with sodium hydroxide which effectively generates monosodium cyanamide in situ.

Suitably, the reaction takes place in the presence of an organic solvent, preferably dimethylformamide or a halogenated hydrocarbon, for example, dichloromethane. The reaction is preferably effected at a temperature in the range from −20° C. to 50° C.

A compound of formula III may be prepared as follows, where Ar is as defined above:

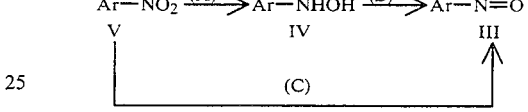

Reaction A may, for example, be effected by reaction of the nitro compound with hydrazine hydrate, in the presence of a hydrogen transfer catalyst, for example rhodium on carbon, suitably in the presence of an inert polar organic solvent, for example, tetrahydrofuran, preferably with cooling; or be effected using water, stannous chloride as reducing agent, an inert, polar organic solvent, for example tetrahydrofuran, under an inert atmosphere, for example nitrogen, in the presence of sodium acetate, suitably at ambient temperature.

Reaction B may suitably be effected by treatment of the hydroxylamine derivative with an oxidising agent, for example an $Fe^{3+}$ compound, suitably ferric chloride. The reaction may be effected in a mixed water/polar organic solvent, preferably with cooling.

Reaction C may be effected by irradiating the nitro compound, which is preferably dissolved in an inert organic solvent, for example benzene. The irradiation may be effected using a medium pressure mercury lamp.

Details of the above processes may be found in applicants' co-pending European patent applications nos. 92120580.3 and TS 8009 EPC. Other methods suitable for preparing compounds of formula I, and further descriptions of the methods described herein, may be found in The Journal of Antibiotics, Jan. 1975, p.87–90 and June 1986, p.864–868; in Eur.J.Med. Chem.-Chim. Ther., 1982, 17, No. 5, p.482–484, and 1980, 15, No.5, p.475–478, and 1977, 12, No.1, p.59–62; in J.Chem. Soc.,Chem. Commun., 1984, p.323–324; in Chem. Ind. (Milan), 1977, 59(5), p.385; in Gazetta Chimica Italiana, 106, 1976, p.1107–1110; in Tetrahedron Letters, No. 38, 1974, p. 3431–3432; and in U.S. Pat. Nos. 4,558,040 and 4,550,121.

The compounds of general formula I have been found to have fungicidal activity. Accordingly, the invention further provides a fungicidal composition which comprises a carrier and, as active ingredient, a compound of formula I as defined above. A method of making such a composition is also provided which comprises bringing a compound of formula I as defined above into association with at least one carrier. Such a composition may contain a single compound or a mixture of several compounds of the present invention.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinires, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing $\frac{1}{2}$–10% w of active ingredient. Granules are usually prepared to have a size between 10 and 100 BS mesh (1.676–0.152 mm), and may be manufactured by agglomeration or impregnation techniques. Generally, granules will contain $\frac{1}{2}$–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penerrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick mayonnaise like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition. A locus as described above may suitably be treated with a compound I at an application rate in the range 0.05 to 4 kg/ha, preferably 0.1 to 1 kg/ha.

The present invention is of wide applicability in the protection of crop plants against fungal attack. Typical crops which may be protected include vines, grain crops such as wheat and barley, apples and tomatoes. The duration of protection is normally dependent on the individual compound selected, and also a variety of external factors, such as climate, whose impact is normally mitigated by the use of a suitable formulation. The invention is further illustrated by the following examples.

Example 1

Preparation of 3-methoxy4-propanamido-1-azoxycyanobenzene (Position of —NHCOR group'4; R32 —$C_2H_5$; $R^1$ =3—$CH_3$; $R^2$=H)

3-Methoxy-4-propanamido-1-nitrosobenzene (2.7 g, 13.0 mmol) and cyanamide (0.51 g, 11.8 mmol) were dissolved in dichloromethane (60 ml). A solution of iodobenzene diacetate (5.34 g, 14.6 mmol) in dichloromethane was added dropwise at 0°–5° C. under nitrogen. The mixture was stirred overnight at ambient termperature, filtered and evaporated to dryness. Column chromatography on silica using 1:1 petroleum ether:ethyl acetate as eluant gave 2.0 g (62% yield) 3-methoxy-4-propanamido-1-azoxycyanobenzene as a yellow powder, m.pt.: 142°–144° C., m/e ($M^+$):248

$^1$H-NMR(CDCl$_3$): δ (ppm)=1.20 (t,CH$_3$); 2.42 (q,CH$_2$);3.93 (s, OCH$_3$); 7.67,7.78,8.55 (m,Ar-H);8.02 (s,NH)

Example 2

Preparation of 3-methoxy-4(2-chloropropanamido)-1-azoxycyanobenzene (Position of —NHCOR group=4:R=—CHCl—CH$_3$; $R^1$=3-OCH$_3$; $R^2$=H)

3-Methoxy-4-(2-chloropropanamido)-1-nitrosobenzene (6.1 g, 25.1 mmol) was dissolved in dichloromethane (100 ml). Cyanamide (1.02 g, 24.3 mmol) and iodobenzene diacetate (8.9 g, 27.6 mmol) were added. The mixture was then stirred for 1 hour at 0° C. and 24 hours at ambient temperature. The resulting yellow suspension was filtered and evaporated to dryness. Column chromatography on silica using toluene as eluant gave 3.4 g (47% yield) 3-methoxy-4-(2-chloropropanamido)-1-azoxycyanobenzene as a yellow solid, m.pt: 151° C., m/e($M^+$): 282/285.

$^1$H-NMR(CDCl$_3$):δ (ppm)=3.92 (s, OCH$_3$); 7.38,7.60–7.90 (m,Ar—H); 8.12 (s,NH)

Example 3

Preparation of 3-propanamido-4-methoxy-1-azoxycyanobenzene (Position of —NHCOR group=3;R=—C$_2$H$_5$; $R^1$=4-OCH$_3$; $R^2$=H)

(a) Preparation of 3-propanamido-4-methoxy-1-azocyanobenzene

3-Propanamido-4-methoxy-1-aminobenzene (3..0 g, 15.4 mmol) was dissolved in a mixture of water (3.8 ml) and hydrochloric acid (4.4 ml, 35% w/w). After the addition of crushed ice (17 g), the solution was diazotised by addition of sodium nitrite (1.09 g, 15.7 mmol). The chilled solution was neutralised with sodium hydroxide (10% w/w), trichloromethane (40 ml) was added and the reaction mixture was cooled to about 0° C. After the addition of potassium cyanide (1.0g, 15.4 mmol) dissolved in water (7.5 ml), the organic layer was separated, dried over sodium sulphate, evaporated to dryness and filtered to give 3.35 g (93.6% yield) 3-propanamido-4-methoxy-1-azocyanobenzene as orange crystals.

(b) Preparation of 3-propanamido-4-methoxy-1-azoxycyanobenzene

The crude 3-propanamido-4-methoxy-1-azocyanobenzene (1.0 g, 4.3 mmol) obtained in (a) above was suspended in a mixture of methanoic acid (10 ml) and hydrogen peroxide (5 ml, 30 wt %). The mixture was heated to 60° C. for 24 hours and then cooled in an ice bath. The resulting crystals were collected and washed with water to give 0.47 g (44% yield) 3-propanamido-4-methoxy-1-azoxycyanobenzene as orange crystals, m.pt: 186°–190° C., m/e($M^+$):248.

$^1$H-NMR(CDCl$_3$): δ (ppm)=1.25(t,CH$_3$-C);2.45(q,COCH$_2$);4.05 (s,OCH$_3$); 6.93,7.98(m,Ar—H);9.35 (s,NH)

Examples 4 to 25

By processes similar to those described in Examples 1 to 3 above, further compounds according to the invention were prepared as detailed in Table I below. In this table the compounds are identified by reference to formula I. Melting point, mass spectroscopy (m/e) and $^1$H-NMR data for the compounds of Examples 4 to 25 are given in Table IA below.

TABLE I (N.B. In all the following examples the group —NHCOR is located at the 4- position of the benzene ring relative to the azoxycyano group.)

| Example No. | R | $R^1$ | $R^2$ |
|---|---|---|---|
| 4 | —CH$_3$ | 3-OCH$_3$ | H |
| 5 | furan-2-yl | 3-OCH$_3$ | H |
| 6 | —$^n$C$_3$H$_7$ | 3-OCH$_3$ | H |
| 7 | —$^i$C$_3$H$_7$ | 3-OCH$_3$ | H |
| 8 | —$^n$C$_5$H$_{11}$ | 3-OCH$_3$ | H |
| 9 | —$^t$C$_4$H$_9$ | 3-OCH$_3$ | H |
| 10 | —CH$_2$Cl | 3-OCH$_3$ | H |
| 11 | —CH=CHCH$_3$ | 3-OCH$_3$ | H |
| 12 | —$^n$C$_4$H$_9$ | 3-OCH$_3$ | H |
| 13 | —CH$_2$COOC$_2$H$_5$ | 3-OCH$_3$ | H |
| 14 | —CH$_3$ | 3-CH$_3$ | H |
| 15 | —CH$_3$ | 3-Cl | 5-Cl |
| 16 | —CH$_3$ | 3-Cl | H |
| 17 | —CH$_2$CH$_2$Cl | 3-OCH$_3$ | H |
| 18 | 2,6-F$_2$ phenyl | 3-OCH$_3$ | H |
| 19 | —CH$_2$CH$_2$Br | 3-OCH$_3$ | H |
| 20 | —CH$_2$CH$_2$-cyclopentyl | 3-OCH$_3$ | H |
| 21 | 3,4,6-(CH$_3$)$_3$cyclohex-3-enyl | 3-OCH$_3$ | H |
| 22 | 3,4,5-(OCH$_3$)$_3$ phenyl | 3-OCH$_3$ | H |
| 23 | —CH$_3$ | 3-CN | H |
| 24 | —C$_2$H$_5$ | 3-CN | H |
| 25 | —$^n$C$_3$H$_7$ | 3-CN | H |

TABLE IA

| Example No. | M.pt. (°C.) | m/e ($M^+$) | $^1$H-NMR(CDCl$_3$):δ(ppm) |
|---|---|---|---|
| 4 | | 234 | 2.23(s, CH$_3$CO); 4.08(s, OCH$_3$); 7.88, 8.02, 8.50(m, Ar—H); 9.80(s, NH) |
| 5 | 155–160 | 286 | 4.05(s, OCH$_3$); 6.58, 7.30, 7.56, 7.78, 7.98, 8.66(m, Ar—H) |
| 6 | 144 | 262 | 1.00, 1.74, 2.40(m, propyl); 3.98(s, OCH$_3$); 7.70, 7.92, 8.58(m, Ar—H); 7.99(s, NH) |
| 7 | 122–125 | 262 | 1.26(d, 2×CH$_3$); 2.60(septet, CH); 3.98(s, OCH$_3$); |

TABLE IA-continued

| Example No. | M.pt. (°C.) | m/e (M+) | 1H-NMR(CDCl3):δ(ppm) |
|---|---|---|---|
| 8 | 118–120 | 290 | 7.70, 7.93, 8.59(m, Ar—H); 8.05(s, NH) 0.88, 1.35, 1.72, 2.42(m, pentyl); 3.98(s, OCH3); 7.69, 7.92, 8.57(m, Ar—H); 8.02(s, NH) |
| 9 | 155–157 | 276 | 1.30(s, t-butyl); 4.02(s, OCH3); 7.72, 7.95, 8.60(m, Ar—H); 8.33(s, NH) |
| 10 | 177–179 | 269/271 | 4.03(s, OCH3); 4.26(CH2Cl); 7.77, 7.89, 8.55(m, Ar—H); 9.20(s, NH) |
| 11 | 184–186 | 260 | 1.95(m, CH3); 4.00(s, OCH3); 6.00, 7.05(m, CH=CH); 7.72, 7.96, 8.68(m, Ar—H); 7.99(s, NH) |
| 12 | 145–147 | 276 | 0.93, 1.38, 1.72, 2.43(m), 3.98(s, OCH3); 7.70, 7.95, 8.60(m, Ar—H); 8.00(s, NH) |
| 13 | 133–136 | 306 | 1.31(t, CH3); 4.25(q, CH2); 4.02(s, OCH3); 7.72, 7.93, 8.55(m, Ar—H); 10.09(s, NH) |
| 14 | 199–203 | 218 | 2.12(s, CH3); 2.32(s, COCH3); 8.10(m, Ar—H); 9.46(s, NH) |
| 15 | 225–226 | | 2.17(s, CH3CO); (35/37Cl) 8.48(s, Ar—H); 10.28(s, NH) |
| 16 | 168–170 | 238/240 | 2.23(s, CH3CO); 8.20-8.40(m, Ar—H); 9.92(s, NH) |
| 17 | 208–211 | | |
| 18 | 202–204 | | |
| 19 | 167–170 | | |
| 20 | 123 | | |
| 21 | 175 | | |
| 22 | 188–193 | | |
| 23 | 195–200 | | |
| 24 | 201 | | |
| 25 | 173–176 | | |

Example 26

The fungicidal activity of compounds of the invention was investigated by means of the following tests.

(a) Direct protectant activity against broad bean grey mould (*Botrytis cinerea*; BCB The test is a direct protectant one using a foliar spray. The upper surfaces of leaves of broad bean plants (cv The Sutton) are sprayed with a solution of the test compound in 1:1 water/acetone containing 0.04% "TWEEN 20" (Trade Mark; a polyoxyethylene sorbitan ester surfactant). Plants are treated using an automated sprayline with an atomising nozzle. The concentration of the compound is 1000 ppm and the spray volume is 700 l/ha. 24 hours after spraying the leaves are inoculated with an aqueous suspension containing $10^5$ conidia/ml. For 4 days after inoculation plants are kept moist in a humidity cabinet at 21° C. Disease is assessed 4 days after inoculation, based on the percentage of leaf surface area covered by lesions.

(b) Activity against tomato early blight (*Alternaria solani*; AS)

This test measures the contact prophylactic activity of test compounds applied as a foliar spray. Tomato seedlings (cv Outdoor Girl) are grown to the stage at which the second true leaf is expanded. The plants are treated using an automated sprayline as described under (a). Test compounds are applied as solutions or suspensions in a mixture of acetone and water (50:50 v/v) containing 0.04% surfactant ("TWEEN 20"—Trade Mark). One day after treatment the seedlings are inoculated by spraying the leaf upper surfaces with a suspension of *A. solani* conidia containing $10^4$ spores/ml. For 4 days after inoculation plants are kept moist in a humidity compartment at 21° C. Disease is assessed 4 days after inoculation, based on the percentage of leaf surface area covered by lesions.

(c) Activity against wheat eyespot in-vitro (*Pseudocercosporella herpotrichoides*; PHI), This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 50 ppm compound and 2.5% acetone. Each compartment is inoculated with a 6 mm diameter plug of agar/myceltum taken from a 14 day old culture of P. herpotrichoides. Plates are incubated at 20° C. for 12 days until the assessment of mycelial growth.

The extent of disease control in all the above tests is expressed as a rating compared with either an untreated control or a diluent-sprayed-control, according to the criteria:

0=less than 50% disease control
1=about 50–80% disease control
2=greater than 80% disease control The results of these tests are set out in Table II below:

TABLE II

| | Fungicidal Activity | | |
|---|---|---|---|
| Example No. | BCB | AS | PHI |
| 4 | 2 | 2 | 2 |

Example 27

The fungicidal activity of compounds of the invention was further investigated by means of the following tests.

(a) Direct protectant activity against tomato late blight (*Phytophthora infestans*; PIP)

The test is a direct protectant one using a foliar spray. Tomato plants with two expanded leaves (cv. First in the Field) are sprayed with a solution of the test compound in 1:1 water/acetone containing 0.04% "TWEEN 20" (Trade Mark; a polyoxyethylene sorbitan ester surfactant). Plants are sprayed using a track sprayer equipped with 2 air-atomising nozzles. The concentration of the compound is 600 ppm and the spray volume is 750 l/ha. After drying, the plants are kept for 24 hours in a glasshouse at 20° C. and 40% relative humidity. The upper surfaces of the leaves are then inoculated with an aqueous suspension containing $2 \times 10^5$ zoosporangia/ml. The inoculated plants are kept for 24 hours at 18° C. in a high humidity cabinet and then for 5 days in a growth chamber at 15° C. and 80% relative humidity with 14 hours light/day. The assessment is based on the percentage of diseased leaf area compared with that on control leaves.

(b) Activity against tomato early blight (*Alternaria solani*; AS)

The test is a direct prophylactic one using a foliar spray. Tomato seedlings (cv Outdoor Girl), at the stage at which the second leaf is expanded, are sprayed with the test compound at a dosage of 600 ppm as described under (a). After drying, the plants are kept for 24 hours in a glasshouse at 20° C. and 40% relative humidity followed by inoculation of the leaf upper surfaces with an aqueous suspension of *A. solani* conidia containing $1 \times 10^4$ conidia/ml. After 4 days in a high humidity cabinet at 21° C., disease is assessed based on the percentage of leaf surface area covered by lesions when compared with control plants.

(c) Direct protectant activity against broad bean grey mould (*Botrytis cinerea*; BCB)

The test is a direct protectant one using a foliar spray. Broad bean plants (cv The Sutton) with two leaf pairs are sprayed with the test compound at a dosage of 600 ppm as described under (a). After drying, the plants are kept for 24 hours in a glasshouse at 20° C. and 40% relative humidity. The upper surface of the leaves are then inoculated with an aqueous suspension containing $1 \times 10^6$ conidia/ml. Plants are kept for 4 days at 22° C. in a high humidity cabinet. The assessment is based on the percentage of diseased leaf area compared with that on control leaves.

(d) Activity against wheat leafspot (*Leptosphaeria nodorum;* LN.)

The test is a direct therapeutic one using a foliar spray. Wheat seedlings (cv Norman), at the single leaf stage, are inoculated with an aqueous suspension containing $1.5 \times 10^6$ conidia/ml. The inoculated plants are kept for 24 hours at 20° C. in a high humidity cabinet followed by spraying with the test compound at a dosage of 600 ppm as described under (a). After drying, the plants are kept for 6–8 days in a glasshouse at 22° C. and 70% relative humidity. Assessment is based on the density of lesions per leaf compared with that on leaves of control plants.

(e) Activity against rice leaf blast (*Pyricularia oryzae;* PO)

The test is a direct therapeutic one using a foliar spray. The leaves of rice seedlings (cv Aichiaishi—about 30 seedlings per pot) are sprayed with an aqueous suspension containing $10^5$ spores/ml 20–24 hours prior to treatment with the test compound. The inoculated plants are kept overnight in high humidity and then allowed to dry before spraying with the test compound at a dosage of 1000 ppm using an automated sprayline as described under (a). After treatment the plants are kept in a rice compartment at 25°–30° C. and high humidity. Assessments are made 4–5 days after treatment and are based on the density of necrotic lesions per leaf when compared with control plants.

(f) Activity against wheat eyespot in-vitro (*Pseudocercosporella herpotrichoides;* PHI)

This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 10 ppm test compound and 0.825% acetone. The fungal inoculum consists of mycelial fragments of *P. herpotrichoides* grown in half strength Potato Dextrose Broth in shaken flasks and added to the broth to provide $5 \times 10^4$ mycelial fragments/ml broth. Petri dishes are incubated at 20° C. for 10 days until the assessment of mycelial growth.

(g) Activity against Rhizoctonia in-vitro (*Rhizoctonia solani:* RSI)

The test measures the in-vitro activity of compounds against *Rhizoctonia solani* that causes stem and root rots. The test compound is dissolved or suspended in acetone and added into 4ml aliquots of half strength Potato Dextrose Broth dispensed in 25-compartment petri dishes to give a final concentration of 10 ppm compound and 0.825% acetone. The fungal inoculum consists of mycelial fragments of *R. solani* grown in half strength Potato Dextrose Broth in shaken culture flasks and added to the broth to provide $5 \times 10^4$ fragments/ml broth. Petri dishes are incubated at 20° C. for 10 days until the assessment of mycelial growth.

(h) Activity against apple scab in-vitro (*Venturia inaequalis;* VII)

This test measures the in-vitro activity of compounds against Venturia inaequalis that causes apple scab. The test compound is dissolved or suspended in acetone and added into 4 ml aliquots of half strength Potato Dextrose Broth dispensed in 25-compartment petri dishes to give a final concentration of 10 ppm compound and 0.825% acetone. The fungal inoculum consists of mycelial fragments and spores of *V. inaequalis* grown on malt agar and added to the broth to provide $5 \times 10^4$ propagules/ml broth. Petri dishes are incubated at 20° C. for 10 days until the assessment of mycelial growth.

The extent of disease control in all the above tests is expressed as a rating compared with either an untreated control or a diluent-sprayed-control, according to the criteria:

0 = less than 50% disease control
1 = 50–80% disease control
2 = greater than 80% disease control The results of these tests are set out in Table III below:

TABLE III

| Example No. | Fungicidal Activity | | | | | | | |
|---|---|---|---|---|---|---|---|---|
| | PIP | AS | BCB | LN | PO | PHI | RSI | VII |
| 1 |  | 2 |  |  |  | 2 | 1 | 2 |
| 2 | 2 | 2 | 1 |  |  | 2 | 1 | 2 |
| 3 | 2 | 2 | 1 |  | 1 | 2 | 1 | 2 |
| 5 |  |  |  |  |  |  |  | 1 |
| 6 |  | 2 | 2 |  |  | 2 | 1 |  |
| 7 |  | 2 | 2 |  |  | 2 |  | 2 |
| 8 |  | 1 |  |  |  | 2 |  | 2 |
| 9 |  | 2 | 2 |  |  | 2 |  | 2 |
| 10 |  | 2 | 2 |  |  | 2 | 2 | 2 |
| 11 |  | 2 | 2 |  |  | 2 | 2 | 2 |
| 12 |  | 2 | 2 |  |  | 2 | 1 | 2 |
| 13 |  | 2 |  | 2 |  | 1 |  | 2 |
| 14 | 2 | 2 | 2 |  | 1 | 2 | 2 | 2 |
| 15 | 2 | 2 | 1 |  |  | 2 | 2 | 2 |
| 16 | 2 | 2 | 2 |  |  | 2 |  | 2 |
| 17 | 2 | 2 | 2 |  |  | 1 | 2 | 2 |
| 18 | 2 |  | 1 |  |  |  |  | 1 |
| 19 | 2 | 2 | 1 |  |  | 1 | 1 | 2 |
| 20 | 1 |  |  |  |  |  |  | 1 |
| 21 | 2 |  | 2 |  |  |  |  |  |
| 22 |  |  |  |  |  |  |  | 2 |
| 23 | 1 |  | 1 |  |  | 2 | 2 | 2 |
| 24 | 1 |  | 1 |  |  | 2 | 2 | 2 |
| 25 | 2 | 2 |  |  | 1 | 2 | 2 | 2 |

I claim:
1. A compound of general formula

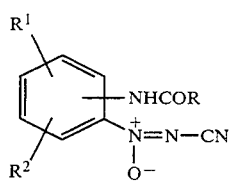

(I)

in which

R represents an optionally substituted alkyl, alkenyl, alkynyl, cycloalkyl, cycloalkenyl, aryl or heterocyclyl group;

$R^1$ represents a halogen atom, nitro, cyano or optionally substituted alkyl, alkoxy, aryl or aryloxy group; and $R^2$ represents a hydrogen or halogen atom, nitro, cyano or optionally substituted alkyl or alkoxy group.

2. A compound according to claim 1 in which R represents a $C_{1-6}$ alkyl, $C_{2-6}$ alkenyl, $C_{2-6}$ alkynyl, $C_{3-8}$ cycloalkenyl or phenyl group or a 3- to 6-membered heterocyclic ring, each group or ring being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, $C_{1-4}$ alkoxycarbonyl and $C_{3-8}$ cycloalkyl groups.

3. A compound according to claim 1 in which $R^1$ represents a halogen atom, a nitro or cyano group, or a $C_{1-6}$ alkyl or $C_{1-6}$ alkoxy group each optionally substituted by one or more substituents selected from halogen atoms, nitro, cyano, hydroxyl and amino groups.

4. A compound according to claim 1 in which $R^2$ represents a hydrogen or halogen atom.

5. A compound according to claim 2 in which R represents a methyl, ethyl, propyl, butyl, pentyl, chloromethyl, chloroethyl, bromoethyl, ethoxycarbonylmethyl, cyclopentylethyl, propenyl, trimethylcyclohexenyl, difluorophenyl, trimethoxyphenyl or furanyl group; $R^1$ represents a chlorine atom or a cyano, methyl or methoxy group; and $R^2$ represents a hydrogen or chlorine atom.

6. A fungicidal composition which comprises a carrier and a compound as defined in claim 1.

7. A composition according to claim 6 which comprises at least two carriers, at least one of which is a surface active agent.

8. A method of combating fungus at a locus which comprises treating the locus with a composition as defined in claim 7.

9. A method according to claim 8 in which the locus comprises plants, subject to or subjected to fungal attack, seeds of such plants or the medium in which the plants are growing or are to be grown.

* * * * *